United States Patent [19]

Cooper

[11] Patent Number: 4,734,498
[45] Date of Patent: Mar. 29, 1988

[54] 3β-SUCCINIMIDOAZETIDINONES AS CHIRAL INTERMEDIATES

[75] Inventor: Robin D. G. Cooper, Indianapolis, Ind.

[73] Assignee: Eli Lilly and Company, Indianapolis, Ind.

[21] Appl. No.: 884,124

[22] Filed: Jul. 10, 1986

[51] Int. Cl.$^4$ .................. C07D 205/08; C07D 405/14; C07D 403/04; C07D 409/14
[52] U.S. Cl. .................................... 540/364; 548/547; 560/171
[58] Field of Search ............................... 540/200, 364

[56] References Cited

PUBLICATIONS

Ikota, Chem. Abs. 102, 78623, (1984).
M. Hatanaka et al., Tetrahedron Letters, vol. 24, No. 44, pp. 4837–4838, 1983.
N. Ikota and A. Hanaka, Heterocycles, vol. 22, No. 10, 1984.

*Primary Examiner*—Mark L. Berch
*Attorney, Agent, or Firm*—William B. Scanlon; Leroy Whitaker

[57] ABSTRACT

3β-Substituted succinimido)azetidinones represented by the formula

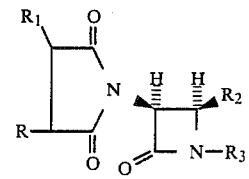

wherein R and $R_1$ are e.g. $C_1$–$C_5$ alkanoyloxy, benzoyloxy, substituted benzoyloxy, or benzyloxy, or one of R and $R_1$ is hydrogen and the other is as defined above; $R_2$ is $C_1$–$C_4$ alkoxycarbonyl or an arylvinyl group e.g. styrryl or 2-furylvinyl; and $R_3$ is e.g. protected-carboxymethyl, or an NH protecting group; are provided via stereoselective cycloaddition of imines with chiral auxiliary 3,4-disubstituted succinimidoacetyl chlorides. The chiral auxiliary e.g., 3S,4S-dibenzoyloxy-and 3S,4S-diacetoxysuccinimidoacetyl chloride, is obtained from tartaric acid via anhydride and imide formation with retention of chirality. The chiral azetidinones obtained are useful intermediates to β-lactam antibacterial compounds.

20 Claims, No Drawings

3β-SUCCINIMIDOAZETIDINONES AS CHIRAL INTERMEDIATES

BACKGROUND OF THE INVENTION

This invention relates to intermediates useful in the preparation of antibiotic compounds. In particular, it relates to chiral azetidinone intermediates useful in the asymmetric synthesis of β-lactam antibiotics.

Many methods have been described for the preparation of β-lactam antibiotics. One such method employs the so-called 2+2 cycloaddition of a ketene with an imine. Recently, considerable work has been directed to the asymmetric preparation of β-lactam compounds with the cycloaddition method e.g., that of N. Ikota and A. Hanaki, *Heterocycles*, Vol. 22, No. 10, 1984, pp. 2227-2230. Furthermore, azetidinone intermediates have been previously used to produce isomers of cephalosporin antibiotics, Doyle et al., *Can. J. Chem.*, 55, 484, 1977. A stereoselective process for preparation of β-lactam antibiotics of the correct stereochemistry would be highly desirable in that cumbersome and expensive resolution steps could be avoided.

SUMMARY 3,4-Dibenzoyloxy(or dialkanoyloxy)succinimidoacetyl halides are useful chiral auxiliary intermediates in the 2+2 cyclocondensation with imines to form stereoselectively azetidinones. For example, 3S,4S-dibenzoyloxysuccinimidoacetyl chloride is condensed with the imine formed with cinnamaldehyde and p-anisidine to form 3-(3S,4S-dibenzoyloxysuccinimido)-4-styryl-1-(4-methoxyphenyl)azetidin-2-one. The cis-azetidinones are useful intermediates for antibacterial β-lactam compounds.

The invention also provides 1-unsubstituted azetidinones substituted in the 3-position by the chiral auxiliary and in the 4-position with a 2-substituted vinyl group, such as the styryl group. These azetidinones also are useful intermediates for β-lactam antibacterials.

DETAILED DESCRIPTION

The intermediate compounds provided by this invention are represented by the formula 1

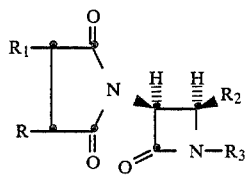

wherein
R and $R_1$ are $C_1$-$C_5$ alkanoyloxy, benzoyloxy, substituted benzoyloxy, benzyl diphenylmethoxy, or triphenylmethoxy; or one of R and $R_1$ is hydrogen and the other is $C_1$-$C_5$ alkanoyloxy, benzoyloxy, substituted benzoyloxy, benzyloxy, diphenylmethoxy, or triphenylmethoxy;
$R_2$ is $C_1$-$C_4$ alkoxycarbonyl or a group represented by the formula

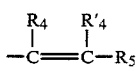

wherein
$R_4$ and $R'_4$ independently are hydrogen or $C_1$-$C_4$ alkyl, $R_5$ is phenyl, naphthyl, m-($C_1$-$C_4$ alkoxy)-phenyl, furyl, or protected carboxy; and
$R_3$ is protected carboxymethyl, an NH protecting group or a 1-(protected carboxy)-2-propanone ketal or thioketal group represented by the formula

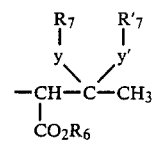

wherein $R_6$ is a carboxy-protecting group, y and y' are oxygen or sulfur, and $R_7$ and $R_7'$ when taken separately are $C_1$-$C_4$ alkyl, and when $R_7$ and $R_7'$ are taken together with the oxygen or sulfur atom to which they are bonded form a 5- or 6-membered ring.

As used herein, the term $C_1$-$C_5$ alkanoyloxy refers to formyloxy, acetoxy, n-propionoxy, n-butryloxy, pivaloyloxy, and like lower alkanoyloxy groups; m-$C_1$-$C_4$ alkoxyphenyl refers to m-methoxyphenyl, m-ethoxyphenyl, m-t-butoxyphenyl, and like $C_1$-$C_4$ alkoxyphenyl ether groups; while the term protected carboxymethyl refers to $C_1$-$C_4$ alkoxycarbonylmethyl, such as methoxycarbonylmethyl, ethoxycarbonylmethyl, t-butoxycarbonylmethyl, and like lower alkyl ester groups; and to carboxymethyl groups wherein the carboxy group is protected by a conventional carboxy-protecting group used for temporary blocking purposes and which is readily removed via hydrolysis or reduction. Such groups include benzyl, 4-methoxybenzyl, 4-nitrobenzyl, diphenylmethyl, 2,2,2-trihaloethyl, and silyl groups e.g., trialkylsilyl such as trimethylsilyl.

The term NH-protecting group refers herein to any group which is generally unreactive during the preparation of the azetidinone ring and which can be subsequently removed to give the NH azetidinone. A number of such groups are known and useful for this purpose. For example, such groups as benzyl, diphenylmethyl, 4-methoxyphenyl, and trialkylsilyl such as t-butyldiethylsilyl are useful.

The term substituted benzoyloxy as used herein refers to a mono- or di-substituted benzoyloxy group substituted by $C_1$-$C_4$ alkyl, $C_1$-$C_4$ alkoxy, halogen, cyano, nitro, amino, or $C_1$-$C_4$ alkoxycarbonyl.

When $R_3$ is a 1-(protected-carboxymethyl)-2-propanone ketal or thioketal group represented by the formula

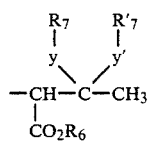

examples of such $R_3$ groups are the acyclic ketal 1-(t-butyloxycarbonylmethyl)-2-propanone dimethyl ketal ($R_6$=t-butyl, y and y'=O, and $R_7$ and $R_7'$ are methyl), the cyclic ketal of the formula

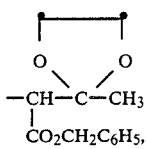

and the cyclic thioketal represented by the formula

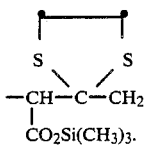

The cyclic ketals wherein y and y' are oxygen are preferred $R_3$ groups of the invention.

The term protected carboxy when used herein refers to the carboxy group temporarily protected or blocked by a conventional protecting group which is readily removed by hydrolysis or reduction. Examples of such groups are t-butyl, 2,2,2-trichloroethyl, 2-iodoethyl, benzyl, 4-methoxybenzyl, 4-nitrobenzyl, diphenylmethyl, trialkylsilyl such as trimethylsilyl and diethyl-t-butylsilyl.

The 3,4-disubstituted succinimido moiety in the 3-position of the azetidinone 1 functions as a chiral auxiliary in the 2+2 cycloaddition formation of the azetidinone ring. This group induces the desired stereochemistry in the 3 and 4 position of the β-lactam ring by virtue of the asymmetric centers to which R and/or $R_1$ are attached. For example, the 3S,4S-disubstituted succinimido affords the 3S,4R-azetidinone whereas the 3R,4R disubstituted succinimido moiety affords the 3R,4S azetidinone.

The azetidinones represented by the formula 1 are prepared via the so-called 2+2 cycloaddition of a 3-substituted or 3,4-disubstituted succinimide derivative capable of forming in situ the succinimido ketene represented by the formula

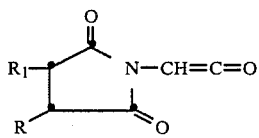

and an imine represented by the formula

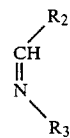

wherein R, $R_1$, $R_2$, and $R_3$ have the same meanings as defined above.

The ketene form of the chiral auxiliary can be generated from the corresponding succinimidoacetyl halide with a base such as a tertiary amine e.g., triethylamine.

The imine used in the cycloaddition reaction is readily obtained by the condensation of the amine $R_3NH_2$ with the aldehyde $R_2$-CHO. For example, the amine and the aldehyde are mixed in dry toluene with molecular sieves to form the imine. Alternatively, the imine can be obtained by azeotropic distillation of the water generated during imine formation.

The cycloaddition reaction is carried out in an essentially anhydrous organic solvent at a temperature between about −80° C. and about 25° C. The cyclocondensation is preferably carried out at a temperature between about −78° C. and about 0° C. The imine and the succinimidoacetyl halide are used in about equimolar amounts, although some excess of either intermediate can be used.

Solvents which can be used include for example, the halogenated hydrocarbons such as methylene chloride, chloroform, trichloroethane and the like; ethers such as tetrahydrofuran and dioxane; nitriles such as acetonitrile and propionitrile; and mixtures of such solvents. A preferred solvent for use in preparing the compounds of the invention is methylene chloride.

A tertiary amine such as a trialkylamine e.g., triethylamine, is employed in the cyclocondensation in an equimolar amount with respect to the chiral auxiliary intermediate. A slight excess of the amine may be used.

The 2+2 addition reaction is generally carried out by adding a solution of the imine to the solution of the ketene which is generated in situ from the amine and the succinimidoacetyl chloride. Following mixing at −78° C., the reaction mixture is warmed to about 0° C. to allow the reaction to finish. The azetidinone product is recovered from the reaction mixture by conventional recovery methods. In general, the mixture is evaporated, the crude product dissolved in a water immiscible solvent such as ethyl acetate, the solution is washed with dilute acid and dilute base, and then dried and evaporated. The product is further purified by crystallization or by chromatography e.g., HPLC.

The succinimidoacetyl halide chiral auxiliary is obtained from tartaric acid or, when one of R and $R_1$ is hydrogen, from malic acid. D-Tartaric acid provides the 3S,4S-disubstituted succinimidoacetyl halide while L-tartaric acid provides the 3R,4R isomer.

The chiral auxiliary is prepared by the acylation or O-alkylation of tartaric acid, treatment of the diacyl or di-O-alkyl tartaric acid with an acid anhydride to form the succinic anhydride, and reaction of the anhydride with an ester of glycine to form first the noncyclic half amide ester which is then cyclized to the 3,4-disubstituted succinimidoacetic acid ester. The ester group is deesterified and the free acid is converted to the acid chloride.

The mono-substituted succinimido chiral auxiliary is obtained with malic acid via succinic anhydride formation followed by succinimide formation as described above.

The preparation of the chiral auxiliary is shown in the following reaction scheme wherein diacetyltartaric acid is used as the starting material.

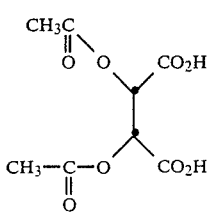

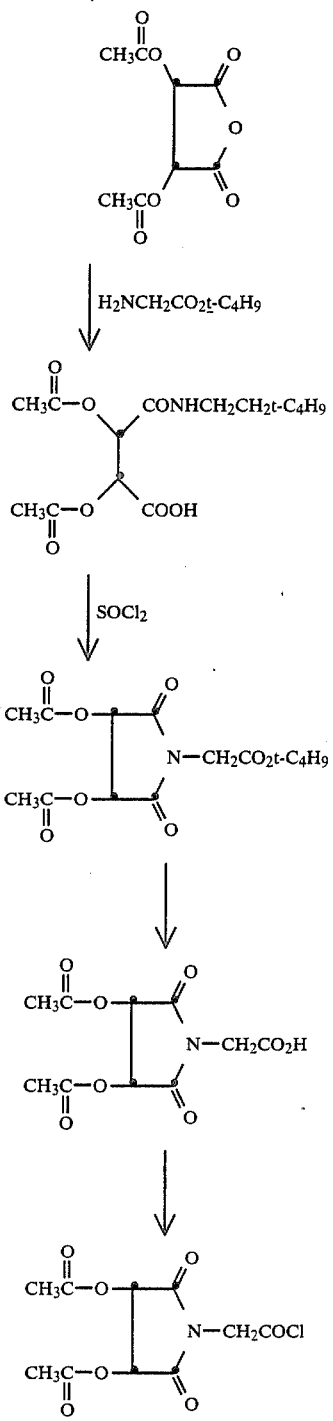

Examples of chiral auxiliary intermediates which can be used to prepare the azetidinones represented by the formula 1 are 3,4-dibenzoyloxysuccinimidoacetyl chloride, 3-benzoyloxysuccinimidoacetyl chloride, 3,4-diacetoxysuccinimidoacetyl chloride, 3-acetoxysuccinimidoacetyl chloride, 3,4-dipropionoxysuccinimidoacetyl chloride, dibenzyloxysuccinimidoacetyl chloride, and 3-diphenylmethoxysuccinimidoacetyl chloride.

The imines used in the 2+2 cycloaddition reaction are prepared as described above by the condensation of the amine $R_3NH_2$ with the aldehyde $R_2$-CHO. Examples of such amines are p-anisidine, benzylamine, methyl glycinate, and t-butyl glycinate. Examples of aldehydes which can be used are cinnamaldehyde, m-methoxycinnamaldehyde, furfuracrolein, t-butyl 3-formylacrylate, benzyl 3-formylacrylate, and diphenylmethyl 3-formylacrylate.

Examples of the β-lactam compounds represented by the formula 1 are 3-(3S,4S-dibenzoyloxysuccinimido-4S-styryl-1-(4-methoxyphenyl)azetidin-2-one, 3-(3S,4S-diacetoxysuccinimido)-4S-styryl-1-(4methoxyphenyl)azetidin-2-one, 3-(3S,4S-dibenzoyloxysuccinimido)-4S-[2-(2-furyl)vinyl]-1-t-butyloxycarbonylmethylazetidin-2-one, 3-(3S,4S-dibenzoyloxysuccinimido)-4S-(2-benzyloxycarbonylvinyl)-1-t-butloxycarbonylmethylazetidin-2-one, 3-(3,4-dibenzyloxysuccinimido)-4-styryl-1-(4-methoxyphenyl) azetidin-2-one, and 3-(3-acetoxysuccinimido)-4-styryl-1-(4-methoxyphenyl)azetidin-2-one.

Preferred compounds of the invention are represented by the formula 1 wherein R and $R_1$ are both benzyloxy, acetoxy or benzoyloxy. Other preferred compounds are represented when $R_2$ is a group represented by the formula

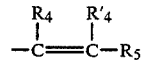

wherein $R_4$ and $R'_4$ are hydrogen and $R_5$ is phenyl, m-methoxyphenyl or furyl. Compounds where $R_3$ is 4-methoxyphenyl are also preferred.

In a further aspect, this invention provides intermediates for antibacterial compounds. The intermediates are represented by the following formula 2

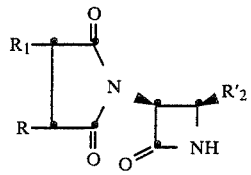

wherein R, and $R_1$ have the same meanings as defined for formula 1 above and $R'_2$ is $R_2$ as defined above, formyl, hydroxymethyl, carboxy, or 2-carboxyethyl.

The intermediates represented by the formula 2 are obtained by the cleavage of a compound represented by the formula 1 wherein $R_3$ is an NH-protecting group e.g., the 4-methoxyphenyl radical. The cleavage of the 4-methoxyphenyl group is carried out with ceric ammonium nitrate in an aqueous medium at a temperature between about −20° C. and about 0° C. The reaction is conveniently carried out in an aqueous medium containing a water miscible solvent such as acetonitrile to at least partially solubilize the azetidinone. A four molar excess of the ceric ammonium nitrate is best used to assure complete removal of the 4-methoxyphenyl radical.

Examples of 1-unsubstituted azetidinones represented by the formula 2 are 3-(3S,4S-dibenzoyloxysuccinimido)-4S-styrylazetidin-2-one, 3-(3S,4S-diacetoxysuccinimido)-4S-[2-(2-furyl)vinyl]azetidin-2-one, 3-

(3,4-dibenzyloxysuccinimido)-4-styrylazetidin-2-one, and 3-(3S,4S-diacetoxysuccinimido)-4-styrylazetidin-2-one, 3-(3,4-dibenzoyloxysuccinimido)-4-methoxycarbonylazetidin-2-one, 3-(3,4-diacetoxysuccinimido)-4-t-butyloxycarbonylazetidin-2-one, 3-(3,4-diacetoxysuccinimido)-4-formylazetidin-2-one, 3-(3,4-dibenzoyloxysuccinimido)-4-hydroxymethylazetidin-2-one, 3-(3,4-diacetoxysuccinimido)-4-(2-carboxyethyl)azetidin-2-one, and 3-(3,4-diacetoxysuccinimido)-4-(2-carboxyethyl)azetidin-2-one.

The compound 2 wherein R'2 is formyl are prepared by the ozonolysis of a compound 2 wherein R'2 is —CH=CHC6H5 as shown in the following scheme

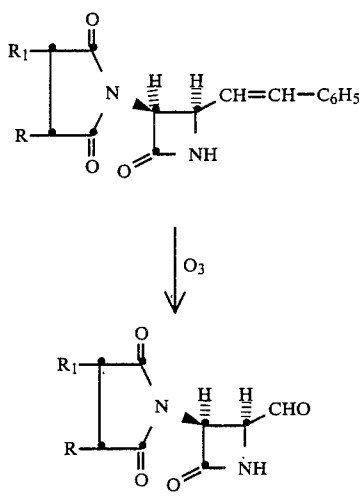

Reduction of the 4-formyl group e.g., with sodium borohydride, provides the corresponding 4-hydroxymethyl azetidinone.

The compound 2 wherein R'2 is 2-carboxyethyl can be obtained by the ozonolysis of the hydrogenation product of a compound 2 wherein R'2 is 2-furylvinyl as shown below.

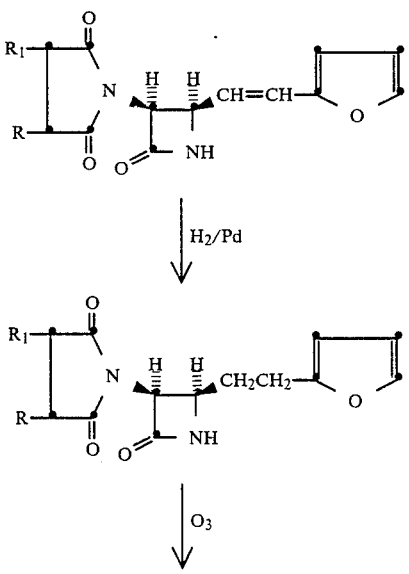

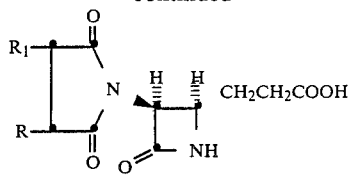

The compounds represented by the formulae 1 and 2 are useful intermediates for known antibacterial compounds. For example, the succinimido chiral auxiliary is removed from the azetidinone in a two-step cleavage reaction to provide the 3β-aminoazetidinone.

According to the cleavage method, the compound represented by the formula 1 or the formula 2 is subjected to basic alcoholysis to form the compound represented by the formula

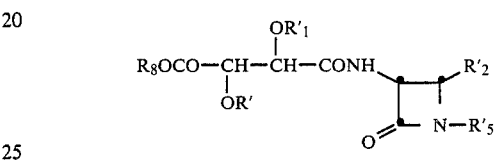

wherein R8 is the residue of the alcohol used in the reaction e.g., R8 is methyl or ethyl when methyl alcohol or ethyl alcohol are used. R' and R'1 are benzyl, diphenylmethyl, triphenylmethyl, or hydrogen; R'2 has the same meanings as defined for formula 2; and R'5 is R3 or hydrogen.

The first step of the cleavage reaction is carried out at about room temperature with sodium methylate/methyl alcohol in THF or with sodium ethylate/ethyl alcohol in THF. The second step comprises the known N-deacylation method used in the N-deacylation of cephalosporin compounds. The intermediate amide obtained in the alcoholysis step is treated with an imino halide forming reagent such as a phosphorus halide e.g., PCl5 to form the imino halide. The latter is converted to the corresponding imino ether upon reaction with an alcohol such as methyl alcohol, isobutyl alcohol or benzyl alcohol. The imino ether then undergoes hydrolysis to the 3β-aminoazetidin-2-one compound represented by the formula

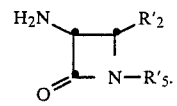

The amino group is protected by substitution with a conventional amino protecting group e.g., benzyloxycarbonyl or t-butyloxycarbonyl and the vinyl group is subjected to oxidative cleavage e.g., ozonolysis to form the 3-protected amino-4-formylazetidin-2-one. The formyl group is reduced by known methods e.g., with sodium borohydride, to form the 4-hydroxymethylazetidinone and the latter is converted to the methanesulfonyloxy ester which upon treatment with sodium iodide form the known 3-iodomethylazetidinone.

The compound represented by the formula 2 wherein R'2 is a m-alkoxystyryl group is converted to 3-hydroxy-1-carbacephalosporins by the method described by D. A. Evans et al., *Tetrahedron Letters*, Vol. 26, No. 32, pp. 3783–3786, 1985; and D. A. Evans et al., ibid pp. 3787–3790.

The 1-benzyl group of the 1-benzylazetidinones can be removed by sodium-liquid ammonia reduction to also provide the compounds represented by the formula 2.

The following Examples are provided to further describe the compounds of the invention and the methods of their preparation.

PREPARATION 1

3S,4S-Dibenzoylsuccinimidoacetic acid chloride (a) 3S,4S-Dibenzoyloxysuccinic anhydride To 1200 ml of acetic anhydride were added 189.5 g (0.5 M) of dibenzoyltartaric acid monohydrate (S,S D+110°) and the solution obtained was stirred for 24 hours at room temperature. The reaction mixture was cooled in the refrigerator, filtered, the product washed with cold acetic anhydride and dried at 40° C., under vacuum. There were obtained 118 g (69% yield) of the succinic anhydride.

A second batch of the anhydride, 29.1 g, was obtained in the same manner with 40 g of dibenzoyloxytartaric acid.

(b) t-Butyl 3S,4S-dibenzoyloxysuccinimidoacetate

The succinic anhydride (a), 103.8 g (305 mmole) was dissolved in 90 ml of methylene chloride and the solution cooled to 0° C. To the cold solution was added dropwise over 30 minutes a solution of 40 g (305 mmole) of t-butyl glycinate in 100 ml of methylene chloride. The mixture was allowed to warm to room temperature and was stirred for 18 hours. The reaction mixture was evaporated to dryness under vacuum to provide the half acid amide of t-butyl glycinate as a foam.

The half acid amide was dissolved in 1 l of benzene, 60 ml of thionyl chloride were added to the solution and the mixture was heated at the reflux temperature for 1 hour. The reaction mixture was then evaporated to dryness and the solid triturated with diethyl ether, the triturate filtered and the filtrate dried. The above process was repeated five times to extract the product from the solid and the final filtrate was poured through silica gel. The product was washed from the silica with methylene chloride containing 1% ethyl acetate. There were obtained 115.6 g (84% yield) of t-butyl 3S,4S-dibenzoyloxysuccinimidoacetate.

(c) 3S,4S-Dibenzoyloxysuccinimidoacetic acid

The t-butyl succinimidoacetate (15 g, 33 mmole) obtained as described above was dissolved in the minimum amount of methylene chloride needed to form a solution. The solution was treated with 15 ml of trifluoroacetic acid and the solution was stirred for 16 hours at room temperature. The solution was evaporated to dryness and the acid product crystallized on standing. The crystalline acid was triturated with cyclohexane containing 5% of diethyl ether, filtered and dried. There were obtained 12.84 g (98% yield) of 3S,4S-dibenzoyloxysuccinimidoacetic acid.

Optical Rotation: $[\alpha]^{25} = -150.70°$ (C=1, CH$_3$OH)

Elemental analysis calculated for $C_{20}H_{15}NO_8$: Theory: C, 60.46; H, 3.81; N, 3.53: Found: C, 60.60; H, 4.08; N, 3.27.

(d) 3S,4S-Dibenzoyloxysuccinimidoacetic acid chloride

The acid (c) obtained as described above, 96 g, (242 mmole) was dissolved in 2 l of methylene chloride and oxalyl chloride (725 mmole, 3 e.q.) was added followed by 1 ml of DMF. The solution was stirred for 3 hours and evaporated to dryness. The solid acid chloride was stirred in a mixture of diethyl ethermethylene chloride, filtered and dried to yield 96.1 g (96% yield) of the acid chloride.

PREPARATION 2

3S,4S-Diacetoxysuccinimidoacetic acid chloride (a) 3S,4S-Diacetoxysuccinic anhydride D-Tartaric Acid (50 g, 333 mmole) and 100 ml of acetic anhydride were mixed and heated to 60° C. until a solution was obtained. The solution was cooled and stirred at room temperature for 16 hours. The product (a) was filtered, washed with diethyl ether and dried. There were obtained 26 g (36% yield) of 3S,4S-diacetoxysuccinic anhydride.

(b) t-Butyl 3S,4S-diacetoxysuccinimidoacetate

To a solution of 21.6 g (100 mmole) of (a) in 200 ml of methylene chloride were added 13.1 g (100 mmole) of t-butyl glycinate and the solution was stirred at room temperature for 24 hours. The reaction mixture was evaporated to dryness to yield 34.7 g of crude half acid amide. The half acid amide was dissolved in 250 ml of benzene, 20 ml of thionyl chloride were added and the solution was heated at the reflux temperature for 45 minutes. The reaction mixture was evaporated to dryness, the residue dissolved in ethyl acetate and the solution washed with a saturated aqueous solution of sodium bicarbonate, with 1 N hydrochloric acid, and with brine. After drying, the solution was evaporated to yield the product as an oil. The oil was chromatographed on silica (Water's Prep-500) with 0–25% ethyl acetate in toluene. There were obtained 16.33 g (50% yield) of the product as an oil which crystallized. The crystals were washed via trituration with diethyl ether.

(c) 3S,4S-Diacetoxysuccinimidoacetic acid

The t-butyl 3S,4S-diacetoxysuccinimidoacetate (b) (8 g, 24 mmole) was dissolved in 15 ml of methylene chloride. 8 ml of trifluoroacetic acid were added and the solution was stirred for 18 hours at room temperature. The solution was evaporated to dryness to 8.3 g of the acid as a foam.

Optical Rotation: $[\alpha]^{25} = -91.7°$ (CH$_3$OH)

(d) 3S,4S-Diacetoxysuccinimidoacetyl chloride

The acid (c) obtained as described above was combined with another batch of the acid prepared in the same manner (13.55 g) and dissolved in 100 ml of methylene chloride. Oxalyl chloride (13 ml) was added to the solution which was then stirred at room temperature for 3 hours. The solution was evaporated to a foam which was azeotroped twice with toluene to provide 14 g (96% yield) of the title compound.

PREPARATION 3

3S-Acetoxysuccinimidoacetyl chloride (a) 3S-Acetoxysuccinic anhydride

S-Malic acid (26.8 g, 200 mmole) was heated at 60° C. with 200 ml of acetic anhydride until a solution was obtained. The solution was cooled to room temperature and stirred for 16 hours. The solution was then evaporated to dryness to yield the anhydride as an oil.

(b) t-Butyl 3S-Acetoxysuccinimidoacetate

To a solution of 31.6 g of the anhydride (a) in 200 ml of methylene chloride was added all at once 26.2 g of t-butyl glycinate and the solution was stirred at room temperature for 16 hours. The solution was evaporated to dryness and the oil obtained was treated with warm methyl alcohol to destroy any remaining anhydride. The methyl alcohol was evaporated and the residue was stirred in benzene with thionyl chloride to provide 54.2 g of (b) as an oil by the method described above in Preparation 2 (b).

(c) 3S-Acetoxysuccinimidoacetyl chloride

The t-butyl ester (b) (3.8 g) was dissolved in 15 ml of methylene chloride, 4 ml of TFA were added, and the solution was stirred for 18 hours at room temperature. The solution was evaporated to dryness and the residue dissolved in ethyl acetate. The solution was washed with a solution of sodium bicarbonate. The pH of the wash was adjusted to 9, the aqueous layer washed three times with ethyl acetate, the pH adjusted to 2, and the acid product extracted with ethyl acetate. The extract was dried and evaporated to yield 510 mg (17% yield) of the acid as an oil. The oil crystallized after standing for 24 hours.

Optical Rotation: $[\alpha]^{25} = -31.34°$ (CH$_3$OH)

The acid (c) (250 mg) was converted to the acid chloride with thionyl chloride as described in the preceding Preparation.

PREPARATION 4

3S,4S-Dibenzyloxysuccinimidoacetyl chloride (a) 3S,4S-Dibenzyloxysuccinic anhydride to a suspension of sodium hydride (4.8 g 60%) in 250 ml of diethyl ether was added dropwise over 30 minutes; a solution of diethyl α-tartrate (12.36 g, 60 mmole) in 60 ml of diethyl ether. The solution was heated at the reflux temperature for 90 minutes and the ether evaporated. Fresh ether was added to the residue and the new solution stirred and the ether removed. This process was repeated eight more times. DMF (200 ml) was added to the final residue, the solution cooled to 0° C. and 14.3 ml (120 mmole) of benzyl bromide was added to the solution over 10 minutes. The solution was stirred for 14 hours at room temperature, filtered and evaporated to dryness. The dibenzylated diester product was obtained as an oil.

The dibenzyloxy diethyl tartrate was saponified as follows. To a solution of 15 g of dibenzyl diethyl tartrate in 60 ml of ethyl alcohol were added 50.8 ml of 2 N sodium hydroxide and the solution was stirred at room temperature for 4 hours. Hydrochloric acid (8.5 ml, 12 N) was added and the solution was evaporated to dryness. Ethyl acetate was added to the residue, the solution filtered and evaporated to dryness. Ethyl acetate was added to the residue, the solution heated, filtered and evaporated to dryness. There were obtained 13 g of the crude dibenzylated tartaric acid as an oil.

The diacid (12.8 g, 38.8 mmole) was dissolved in 100 ml of acetic anhydride and the solution was stirred for 20 hours. The solution was evaporated to dryness to yield the crude anhydride as an oil. The oil was dissolved in diethyl ether and pentane was added to the solution. The anhydride product crystallized, the crystals filtered and recrystallized from hot diethyl ether/pentane. There were obtained 8.2 g (68% yield) of crystalline 3S,4S-dibenzyloxysuccinic anhydride.

(b) t-Butyl 3S,4S-dibenzyloxysuccinimidoacetate

To a solution of the anhydride (a) (8.1 g, 25.9 mmole) in 100 ml of methylene chloride were added 4.8 g of t-butyl glycinate and the solution was stirred for 3 hours at room temperature. The solution was then evaporated to dryness to an oil which crystallized. The crystalline residue was stirred with diethyl ether and filtered to yield 11.5 g of the half acid amide.

The half acid amide (11.5 g, 26 mmole) was dissolved in 120 ml of benzene, 7.2 ml of thionyl chloride were added and the solution was heated at the reflux temperature for 1.5 hour. The solution was evaporated to dryness, the residue dissolved in ethyl acetate and the solution washed three times with 1 N HCl, twice with an aqueous saturated solution of sodium bicarbonate, once again with 1 N HCl, once with brine, was dried and evaporated to an oil. The oil was crystallized from diethyl ether-Skellysolve B. The product was dissolved in diethyl ether-Skellysolve B, 1—1, v—v and poured through silica. The filtrate was evaporated to dryness. The product, t-butyl 3S,4S-dibenzyloxysuccinimidoacetate was obtained as a yellow oil, 9.5 g (86% yield).

(c) 3S,4S-Dibenzyloxysuccinimidoacetic acid

The acid was obtained by deesterification of the t-butyl ester (b) (9.5 g) with TFA as described in the preceding Preparations. There were obtained 6.9 g (84% yield) of the acid.

The acid (6.9 g) was converted to the acetyl chloride with oxalyl chloride as described above. There were obtained 6.77 g (93% yield) of the acid chloride.

EXAMPLE 1

3β-(3S,4S-Dibenzoyloxysuccinimido)-4β-styryl-1-(4-methoxyphenyl)azetidin-2-one

A solution of 3.1 g (7.56 mmole) of 3S,4S-dibenzoyloxysuccinimidoacetyl chloride in 175 ml of dry methylene chloride was added dropwise with stirring to a solution of 1.7 g (7.18 mmole) of the imine formed with p-methoxyaniline and cinnamaldehyde in methylene chloride containing 1 ml of triethylamine. The solution obtained was stirred for 90 minutes at room temperature, then evaporated to dryness and the residue dissolved in ethyl acetate. The solution was washed with 1 N HCl, a saturated aqueous solution of sodium bicarbonate, again with 1 N HCl, and with brine. The solution was dried and evaporated to dryness. The title compound was obtained as a solid which was crystallized from methylene chloride-diethyl ether to yield 900 mg of first crop material of one isomer and a second crop shown by HPLC analysis to be a 50/50 mixture of isomers.

EXAMPLE 2

3S-(3S,4S-Dibenzoyloxysuccinimido)-4R-[2-(2-furyl)vinyl]-1-t-butyloxycarbonylmethylazetidin-2-one To a solution of 1.9 g (8.1 mmole) of the imine formed with t-butyl glycinate and 2-furylacrolein in 20 ml of dry methylene chloride containing 1.2 ml (8.4 mmole) of triethylamine was added dropwise over 2 minutes a solution of 3.5 g of 3S,4S-dibenzoyloxysuccinimidoacetyl chloride in 100 ml of methylene chloride. The reaction mixture was stirred for about 16 hours and then evaporated to dryness. The residue was dissolved in ethyl acetate and the solution washed twice with 1 N HCl, three times with saturated aqueous sodium bicarbonate, once again with 1 N HCl, twice with brine, was dried and evaporated to dryness. The solid product weighed 5.2 g. The product was dissolved in methylene chloride and cyclohexane was added until the solution was turbid. On standing the title compound crystallized. There were obtained 1.17 g (23% yield).

Mass Spectrum: 614

Optical Rotation: +87.6 (CHCl$_3$, C=10 mg/ml)

Elemental analysis calculated for C$_{33}$H$_{30}$N$_2$O$_{10}$: Theory: C, 64.49; H, 4.92; N, 4.56: Found: C, 64.26; H, 5.01; N, 4.33.

EXAMPLE 3

3S-(3S,4S-Dibenzoyloxysuccinimido)-4R-styryl-1-(4-methoxyphenyl)azetidin-2-one To a solution of 6.77 g (17 mmole) of 3S,4S-dibenzyloxysuccinimidoacetyl chloride in 75 ml of methylene chloride cooled to −78° C. was added dropwise 3.8 ml of triethylamine and the solution was stirred for 10 minutes. To the cold solution was added dropwise over 15 minutes with stirring a solution of 4.8 g (20.3 mmole) of the imine formed with 4-methoxyaniline and cinnamaldehyde in methylene chloride. Following addition of the imine, the reaction mixture was warmed to 0° C., stirred for 2 hours and quenched by the addition of a 0.25 M solution of tartaric acid. The organic layer was separated, evaporated to dryness and the residue dissolved in ethyl acetate. The solution was washed seven times with 1 N HCl, twice with saturated aqueous sodium bicarbonate, once again with 1 N HCl, once with brine and was dried and evaporated to dryness. There were obtained 9.5 g of crude product as a foam. The product was purified via preparative HPLC which yielded 6.1 g of a mixture of isomers in a ratio of about 85–99/−15–10 of the 3S,4R to 3R,4S isomers by weight.

EXAMPLE 4

3S-(3S,4S-Diacetoxy)-4R-styryl-1-(4-methoxyphenyl)azetidin-2-one

To a solution of 14 g (48 mmole) of 3S,4S-diacetoxysuccinimidoacetyl chloride in 150 ml of methylene chloride containing 10 ml of triethylamine and cooled to -78° C. was added dropwise a solution of 10 g (43 mmole) of the imine formed with 4-methoxyaniline and cinnamaldehyde in methylene chloride. The reaction mixture was allowed to warm to 0° C. for 2 hours and the reaction quenched by the addition of 0.25 M tartaric acid. The organic layer was separated and evaporated to dryness. The residue was dissolved in ethyl acetate and the solution was washed with 1 N HCl and sodium bicarbonate solution, dried and evaporated to dryness to yield 10 g of crude product. The product was purified via preparative HPLC using 0–25% ethyl acetate in toluene. There were obtained 7.7 g (37%) of crystalline product comprising both the 3S,4R and the 3R,4S isomers in a ratio of about 70/30 by weight.

Mass Spectrum: 492

Elemental analysis calculated for $C_{26}H_{24}N_2O_8$: Theory: C, 63.41; H, 4.91; N, 5.69: Found: C, 63.61; H, 5.09; N, 5.57.

EXAMPLE 5

3S-(3-Acetoxysuccinimido)-4R-styryl-1-(4-methoxyphenyl)azetidin-2-one

The title compound was prepared by following the procedure and conditions employed in Example 4 when 280 mg of 3-acetoxysuccinimidoacetyl chloride was reacted in methylene chloride in the presence of triethylamine with 480 mg of the Schiff's base formed with p-anisidine and cinnamaldehyde. There were obtained 450 mg of the crude azetidinone which crystallized on standing for two days. The crystalline product was a mixture of isomers in a ratio of about 55/45 by weight (NMR).

Mass Spectrum 434

Elemental analysis calculated for $C_{24}H_{22}N_2O_6$: Theory: C, 66.35; H, 5.10; N, 6.45: Found: C, 66.08; H, 4.85; N, 6.54.

EXAMPLE 6

3-(3S,4S-Dibenzoyloxy)-4-[2-(benzyloxycarbonyl)-vinyl]-1-t-butyloxycarbonylmethylazetidin-2-one To a suspension of 1.19 g (2.86 mmole) of 3S,4S-dibenzoyloxysuccinimidoacetyl chloride in methylene chloride cooled to −78° C. was added 434 μl of triethylamine and the solution obtained was stirred for 15 minutes. Then 0.788 mg (2.6 mmole) of the imine formed with t-butyl glycinate and the benzyl ester of 3-formylacrylic acid was added to the solution. The solution was stirred at −78° C. for 2 hours then was allowed to warm to room temperature. The solution was evaporated to dryness to yield the crude product mixture as a solid. The solid was dissolved in ethyl acetate and the solution washed twice with 1 N HCl, twice with a saturated aqueous solution of sodium bicarbonate, once again with 1 N HCl, with brine, and was dried and evaporated to dryness. There were obtained 1.69 g of the crude product as a foam. The product was purified via preparative HPLC to provide 820 mg (46% yield) of purified product, a mixture of the two isomers in a ratio of 74:26 (HPLC) of 3S,4R:3R,4S.

Mass Spectrum, Field Desorption: 683

Optical Rotation: −96.73°

Elemental analysis calculated for $C_{37}H_{34}N_2O_{11}$: Theory: C, 65.10; H, 5.02; N, 4.10: Found: C, 65.25; H, 5.24; N, 4.07.

EXAMPLE 7

3β-Amino-4β-[2-(2-furyl)vinyl]-1-t-butyloxycarbonylmethylazetidin-2-one

To a solution of 400 mg (0.65 mmole) of 3S-(3S,4S-dibenzoyloxysuccinimido)-4R-2-(2-furyl)vinyl]-1-t-butyloxycarbonylmethylazetidin-2-one in 6 ml of a 50–50 mixture of THF and methyl alcohol were added 52.8 mg (0.98 mmole) of sodium methylate and the solution was stirred for 20 hours at room temperature. The solution was evaporated to dryness, the residue dissolved in ethyl acetate and the solution washed three times with 1 N HCl, twice with saturated aqueous sodium bicarbonate, twice with brine and was then evaporated to dryness. The product (foam) was dissolved in 10% Skellysolve B/diethyl ether and absorbed on silica. The product was eluted with the same solvent mixture to yield 180 mg of the methanolysis product represented by the formula

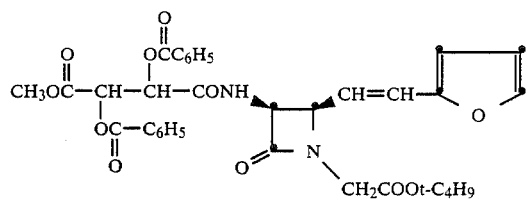

The above intermediate, 180 mg, was dissolved in 5 ml of methylene chloride and 28 μl of pyridine and 6.7 mg of phosphorus pentachloride were added to the solution. After stirring for 1 hour, the NMR spectrum of an aliquot of the reaction mixture showed complete conversion to the imino chloride. The reaction mixture was treated with 193 μl of isobutyl alcohol and stirred for 2 hours. The reaction mixture was evaporated to dryness and the residue washed three times with n-heptane. The residue was dissolved in ethyl acetate and the solution washed with saturated aqueous sodium bicarbonate and with 1 N HCl. The aqueous acidic wash was separated, slurried with ethyl acetate and the pH adjusted to 10. The ethyl acetate was separated, dried and evaporated to dryness. The 3-aminoazetidinone product residue was dissolved in ethyl acetate and poured through silica. The eluate was evaporated to dryness to yield 3.4 mg (4.2% yield) of the title compound as one isomer.

Mass Spectrum 292

EXAMPLE 8

3-(3S,4S-Dibenzoyloxysuccinimido)-4S-styrylazetidin-2-one 3-(3S,4S-Dibenzoyloxysuccinimido)-4S-styryl-1-(4-methoxyphenyl)azetidin-2-one (10 g, 16.2 mmole) was suspended in a mixture of 170 ml of water and 230 ml of acetonitrile and the suspension was cooled to about $-12°$ C. to $-15°$ C. To the cold suspension was added dropwise over 1 hour a solution of 36 g (66.2 mmole) of ceric ammonium nitrate in 60 ml of water. The mixture was stirred for 15 minutes at $-15°$ C., warmed to $0°$ C. and stirred for 15 minutes. The solution was washed four times with 200 ml portions of ethyl acetate, the washes combined and washed twice with water. The ethyl acetate solution was slurried with 200 ml of 1 N HCl and sodium sulfite was added until the orange color had disappeared. The slurry was stirred for 45 minutes, the organic phase separated, washed twice with water, twice with brine, dried and evaporated to dryness yielding 10 g of crude product as a foam. The product was dissolved in methylene chloride and hexane was added to the solution to provide 8.3 g of the title compound as a yellowish precipitate.

Optical Rotation: $-18.53°$ (C=1, $CH_3OH$).

Mass Spectrum: 510

Elemental analysis calculated for $C_{29}H_{22}N_2O_7$: Theory: C, 68.23; H, 4.34; N, 5.49: Found: C, 68.06; H, 4.06; N, 5.76.

I claim:

1. The compound of the formula wherein

R and $R_1$ are $C_1$-$C_5$ alkanoyloxy, benzoyloxy, a mono- or di-substituted benzoyloxy group substituted by $C_1$-$C_4$ alkyl, $C_1$-$C_4$ alkoxy, halogen, cyano, nitro, amino, or $C_1$-$C_4$ alkoxy carbonyl, benzyloxy, diphenylmethoxy, or triphenylmethoxy; or one of R and $R_1$ is hydrogen and the other is $C_1$-$C_5$ alkanoyloxy, benzoyloxy, a substituted benzoyloxy group as defined above, benzyloxy, diphenylmethoxy or triphenylmethoxy;

$R_2$ is $C_1$-$C_4$ alkoxycarbonyl or a grop represented by the formula $$-\overset{R_4}{\underset{|}{C}}=\overset{R'_4}{\underset{|}{C}}-R_5$$

wherein $R_4$ and $R'_4$ independently are hydrogen or $C_1$-$C_4$ alkyl, $R_5$ is phenyl, naphthyl, m-($C_1$-$C_4$ alkoxy) phenyl, furyl, or protected carboxy; and $R_3$ is protected-carboxymethyl, an NH protecting group or a 1-(protected carboxy)-2-propanone ketal or thioketal group represented by the formula $$-CH-\underset{\underset{CO_2R_6}{|}}{\overset{\overset{R_7\ \ \ R'_7}{|\ \ \ \ |}}{\underset{y\diagdown\ \ \diagup y'}{C}}}-CH_3$$

wherein $R_6$ is a carboxy-protecting group, y and y' are both oxygen or sulfur, and $R_7$ and $R_7'$ when taken separately are $C_1$-$C_4$ alkyl, and when taken together are $-CH_2-CH_2-$ or $-CH_2-CH_2-CH_2-$ which with the oxygen or sulfur atoms to which they are bonded form a 5- or 6-membered ring.

2. The compound of claim 1 wherein R and $R_1$ are benzoyloxy, acetoxy, or benzyloxy.

3. The compound of claim 1 wherein $R_3$ is 4-methoxyphenyl.

4. The compound of claim 1 wherein $R_2$ is a group of the formula $$-\overset{R_4}{\underset{|}{C}}=\overset{R'_4}{\underset{|}{C}}-R_5.$$

5. The compound of claim 2 wherein $R_2$ is $C_1$-$C_4$ alkoxycarbonyl.

6. The compound of claim 4 wherein $R_5$ is phenyl, m-methoxyphenyl, or furyl.

7. The compound of claim 6 which is 3β-(3S,4S-dibenzoyloxysuccinimido)-4β-styryl-1-(4-methoxyphenl)azetidin-2-one.

8. The compound of claim 6 which is 3β-(3S,4S-diacetoxysuccinimido)-4β-styryl-1-(4-methoxyphenyl)azetidin-2-one.

9. The compound of claim 6 which is 3β-(3,4-dibenzyloxysuccinimido)-4β-styryl-1-(4-methoxyphenyl)azetidin-2-one.

10. The compound of claim 1 wherein $R_3$ is protected carboxymethyl.

11. The compound of claim 10 which is 3β-(3S,4S-dibenzoyloxysuccinimido)-4β-styryl-1-t-butyloxycarbonylmethylazetidin-2-one.

12. The compound of claim 10 which is 3β-(3S,4S-dibenzoyloxysuccinimido)-4β-[2-(2-furyl)vinyl]-1-t-butyloxycarbonylmethylazetidin-2-one.

13. The compound of claim 10 which is 3β-(3S,4S-dibenzoylsuccinimido)-4β-(2-benzyloxycarbonylvinyl)-1-t-butyloxycarbonylmethylazetidine-2-one.

14. The compound of the formula

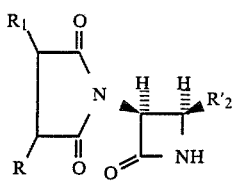

wherein
R and $R_1$ are $C_1$–$C_5$ alkanoyloxy, benzoyloxy, a substituted benzoyloxy group substituted by $C_1$–$C_4$ alkyl, $C_1$–$C_4$ alkoxy, halogen, cyano, nitro, amino, or $C_1$–$C_4$ alkoxy carbonyl, benzyloxy, diphenylethoxy or triphenylmethoxy; or one of R and $R_1$ is hydrogen and the other is $C_2$–$C_5$ alkanoyloxy, benzoyloxy, substituted benzoyloxy group as defined above, benzyloxy, diphenylmethoxy or triphenylmethoxy;

$R'_2$ is $C_1$–$C_4$ alkoxycarbonyl, carboxy, formyl, hydroxymethyl, 2-carboxyethyl, or a group of the formula

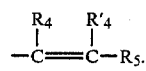

wherein $R_4$ and $R'_4$ independently are hydrogen or $C_1$–$C_4$ alkyl, and $R_5$ is phenyl, naphthyl, m-($C_1$–$C_4$ alkoxy)phyenyl, furyl or protected carboxy.

15. The compound of claim 14 wherein R and $R_1$ are benzoyloxy, acetoxy or benzyloxy.

16. The compound of claim 15 wherein $R_2$ is a group of the formula $$-\underset{\underset{R_4}{|}}{C}=\underset{\underset{R'_4}{|}}{C}-R_5.$$

17. The compound of claim 16 wherein $R_5$ is phenyl, m-($C_1$–$C_4$ alkoxy)phenyl or furyl.

18. The compound of claim 16 which is 3β-(3S,4S-dibenzoyloxysuccinimido)-4S-styrylazetidin-2-one.

19. The compound of claim 14 wherein $R'_2$ is $C_1$–$C_4$ alkoxycarbonyl, hydroxymethyl or 2-carboxyethyl.

20. The compound of claim 19 which is 3β-(3S,4S-dibenzoyloxysuccinimido)-4S-(2-carboxyethyl)azetidin-2-one.

* * * * *